United States Patent [19]

Asai et al.

[11] 4,182,889
[45] Jan. 8, 1980

[54] PROCESS FOR PREPARING 10-METHYL-2,9-DIOXATRICYCLO[4,3,1,0$^{3,7}$] DECANES

[75] Inventors: Akiji Asai, Wennigsen; Ivan Ban, Hanover; Samuel David, Hanover; Peter W. Thies, Hanover, all of Fed. Rep. of Germany

[73] Assignee: Kali-Chemie Pharma GmbH, Hanover, Fed. Rep. of Germany

[21] Appl. No.: 826,636

[22] Filed: Aug. 22, 1977

[30] Foreign Application Priority Data

May 4, 1977 [DE] Fed. Rep. of Germany ....... 2719916

[51] Int. Cl.$^2$ ............................................. C07D 493/08
[52] U.S. Cl. ........................... 546/197; 260/326.11 R; 260/326.5 CA; 260/340.3; 424/267; 544/148; 544/364; 544/378
[58] Field of Search .................... 260/293.58, 268 TR, 260/326.11 R, 326.5 CA, 340.3; 544/148, 378, 364; 546/197

[56] References Cited

U.S. PATENT DOCUMENTS 3,812,154  5/1974  Thies ................................. 260/340.3

FOREIGN PATENT DOCUMENTS 2129507  12/1972  Fed. Rep. of Germany .
1436821   5/1976  United Kingdom .

OTHER PUBLICATIONS

*Chemical Abstracts*, 80: 133654q (1974) [German Offen. 2,340,160; Bernauer et al., 2/21/74].

House, H., *Modern Synthetic Reactions*, 2nd. Ed., W. A. Benjamin, Inc., Menlo Park, Cal., 1972, p. 31.
Migrdichian, V., *Organic Synthesis*, vol. 1, Reinhold Pub. Corp., New York, 1957, p. 465.
March, J., *Advanced Organic Chemistry*, McGraw Hill, New York, 1968, pp. 591-592.
Schroter, R., in *Newer Methods of Preparative Organic Chemistry*, Interscience, New York, 1948, p. 92.

*Primary Examiner*—Alan L. Rotman
*Assistant Examiner*—Richard A. Schwartz
*Attorney, Agent, or Firm*—Schwartz, Jeffery, Schwaab, Mack, Blumenthal & Koch

[57] ABSTRACT

A process for preparing 10-methyl-2,9-dioxatricyclo[4,3,1,0$^{3,7}$] decane derivatives is disclosed, wherein a 10-methylen-3-iodomethyl compound of the formula

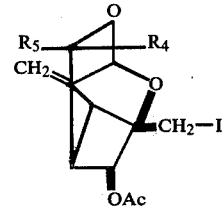

is hydrogenated to obtain a mixture of the corresponding epimeric 10β- and 10α-methyl-3-iodomethyl compounds, the pure 10α- and 10β-methyl epimers are separated and recovered from this mixture and are reacted with a secondary amine. Optionally, the substituent in the 4-position of the resulting 10α- or 10β-methyl-3-aminomethyl compounds are further changed.

17 Claims, No Drawings

PROCESS FOR PREPARING 10-METHYL-2,9-DIOXATRICYCLO[4,3,1,0³,⁷] DECANES

BACKGROUND OF THE INVENTION

The present invention pertains to a process for preparing 10α- and 10β-methyl-3-aminomethyl-2,9-dioxatricyclo[4,3,1,0³,⁷] decanes having the formula I

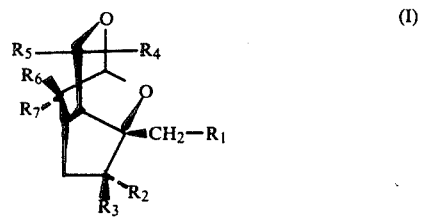

wherein R₁, R₂, R₃, R₄, R₅, R₆ and R₇ are as defined below.

Such dioxatricyclo decanes are disclosed in copending U.S. patent application Ser. No. 770,055, the disclosure of which is hereby incorporated by reference. That U.S. patent application discloses a process for preparing the compounds for formula I according to the following general reaction sequence:

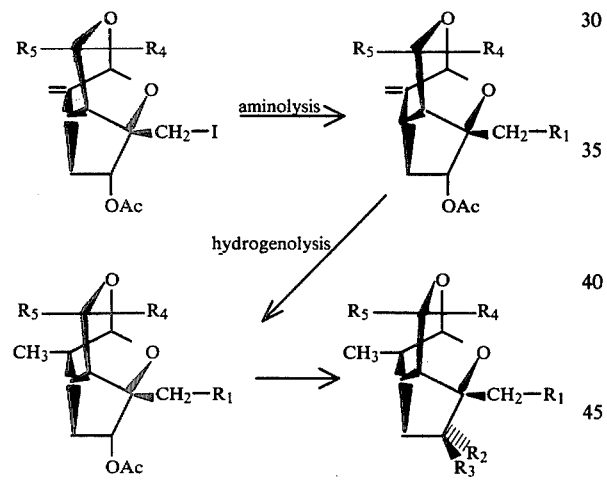

In this process, a halomethyl derivative is first submitted to an aminolysis in the 3'-position, subsequently the 10,11-double bond in the resulting amine is hydrogenated, and then optionally the substituent in the 4-position is further changed.

During the hydrogenation of the 10,11-double bond of the intermediate amine, a mixture of the epimeric 10β- and 10β-methyl compounds are formed, which comprises about 90% of the 10β-methyl compound and about 10% of the 10α-methyl compound. This amine mixture is an oily product which can be crystallized only with great difficulties or not at all. From this mixture, the pure 10β- or 10α-methyl compounds can be recovered only with difficulties and with a certain loss of material.

SUMMARY OF THE INVENTION

It is an object of the present invention to provide a process for preparing 10β- and 10α-methyl-3-aminomethyl-2,9-dioxatricyclo[4,3,1,0³,⁷] decanes wherein a high yield of the pure 10β- and 10α-methyl epimers is obtained.

It is a further object of the present invention to provide such a process wherein the mixture of 10β- and 10α-methyl compounds can easily be separated into the epimers without any substantial loss of material.

In order to accomplish the foregoing objects according to the present invention there is provided a method for preparing 2,9-dioxatricyclo[4,3,1,0³,⁷] decane derivatives of the formula I

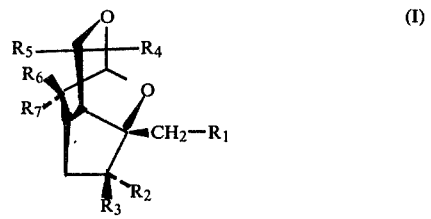

wherein
R₁ represents a tertiary amino group,
one of R₂ and R₃ is hydrogen and the other represents hydroxy, acyloxy or carbamyloxy or R₂ and R₃ jointly represent oxygen,
one of R₄ and R₅ is hydrogen and the other represents alkyloxy or aralkyloxy, and
one of R₆ and R₇ is hydrogen and the other represents methyl, and their pharmacologically acceptable salts.

According to the method of the present invention, tertiary amines of formula Ia

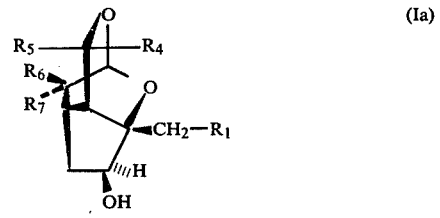

wherein R₁, R₄, R₅, R₆ and R₇ are as defined above, are prepared by a process which comprises the steps of
(a) catalytically hydrogenating a compound of formula III

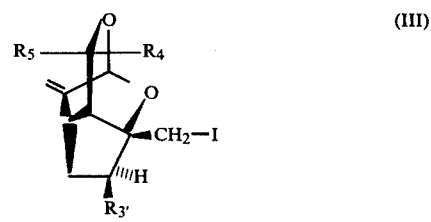

wherein R₃, represents acetoxy and R₄ and R₅ are as defined above,
to form a mixture of epimeric compounds of formula IV

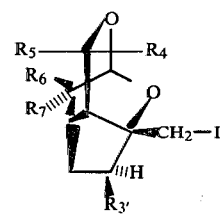

wherein $R_{3'}$, $R_4$, $R_5$, $R_6$ and $R_7$ are as defined above, comprising a 10α-methyl epimer of formula IVa and a 10β-methyl epimer of formula IVb

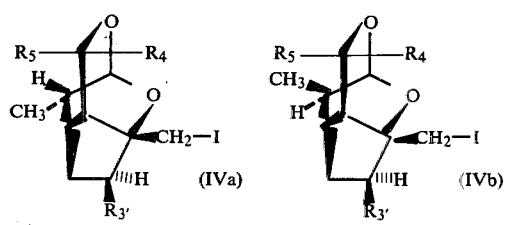

wherein $R_{3'}$, $R_4$ and $R_5$ are as defined above;

(b) separating the compounds of formula IVb and IVa from said mixture;

(c) recovering at least one of the compounds of formula IV substantially free from its epimer;

(d) reacting said compound of formula IV with a secondary amine $R_1$, whereby a reaction mixture comprising the compound of formula Ia substantially free from its epimer is obtained; and, (e) recovering the compound of formula Ia from said reaction mixture.

The aminolysis of the compounds of formula IV may be performed according to known methods. For example, the halomethyl compounds of formula IV are reacted directly with an appropriate secondary amine. The reaction may be performed in the presence of an aminolysis catalyst preferably in the presence of an aprotic solvent which may be the secondary amine itself.

The acetoxy group $R_3$, in the compounds of formula IV is hydrolyzed during the aminolysis or at the latest, during the recovering step, so that the 4-hydroxy compound of formula Ia is obtained.

Prior to the aminolysis, the compound of formula IV may be hydrolyzed in a conventional manner to form the corresponding 4β-hydroxy compound which may be oxidized into the 4-keto compound of formula IVd

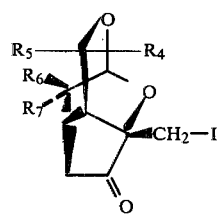

wherein $R_4$, $R_5$, $R_6$ and $R_7$ are as defined above, which in turn may be reduced with a metal hydride, e.g., Li(AlH$_4$) to give the 4α-hydroxy compound of formula IVe

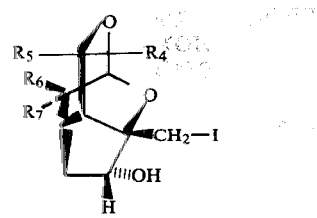

wherein $R_4$, $R_5$, $R_6$ and $R_7$ are as defined above.

Upon aminolysis, the compounds of formula IVd and of formula IVe yield the corresponding amino compounds of formula Ic and Id, respectively.

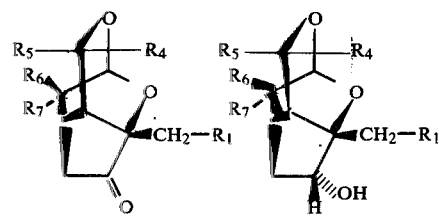

Subsequent to the introduction of amino groups into the compounds of formula IV or IVe, the substituent in the 4-position may be further changed in order to obtain any of the above defined substituents $R_2$ and $R_3$. For example, compounds of formula If

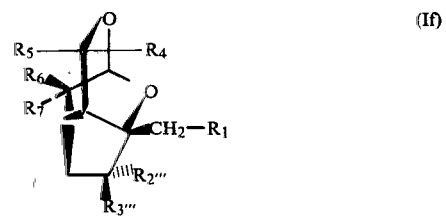

wherein $R_1$, $R_4$, $R_5$, $R_6$ and $R_7$ are as defined in formula I, and one of $R_{2'''}$ and $R_{3'''}$ is hydrogen and the other represents acyloxy or carbamyloxy, can be prepared by esterifying a compound of formula Ig

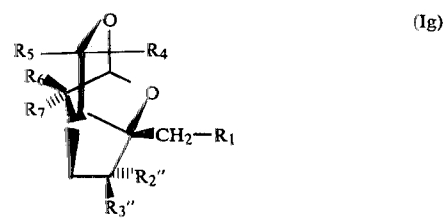

wherein $R_1$, $R_4$, $R_5$, $R_6$ and $R_7$ are as defined in formula I, and one of $R_{2''}$ and $R_{3''}$ is hydrogen and the other is hydroxyl.

The esters are prepared by conventional methods, e.g., reacting the alcohols of formula Ig with appropriate acid halides or isocyanates, respectively. If the substituent $R_1$ comprises a hydroxy group, this group is also esterified during the reaction.

Further objects, features and advantages of the present invention will become apparent from the detailed description of the invention which follows.

DETAILED DESCRIPTION OF THE INVENTION

Surprisingly it has been found that in the iodomethyl compounds of formula III, the double bond in the 10,11-position can be selectively hydrogenated without splitting off the halogen in the 3'-position and/or the acetoxy group in the 4-position, and that the 10β-methyl epimer of the hydrogenation product, that is the 3-iodomethyl-4-acetoxy-10β-methyl-2,9-dioxatricyclo[4,3,1,0$^{3,7}$] decanes of formula IVb, crystallize particularly easily. Accordingly, a simple separation of the 10-methyl epimers IVa and IVb can be achieved.

The process according to the present invention essentially distinguishes from the process which is disclosed in the U.S. patent application Ser. No. 770,055 in that the sequence of the steps of aminolyzing and hydrogenating is reversed.

The hydrogenation of the compounds of formula III is effected by means of hydrogen in the presence of a platinum oxide catalyst in known manners. For example, the reaction is effected in a neutral medium using a neutral solvent.

For recovering the compounds of formula IV from the resulting hydrogenation mixture, the catalyst is separated from the mixture, e.g., by filtration, and then the solvent is evaporated. From the remaining residue, the 10β-methyl derivative of formula IVb may be recovered first by recrystallizing the residue from methanol. The resulting crystallizate is repeatedly recrystallized from methanol for several times.

The 10α-methyl derivative of formula IVa may then be recovered by evaporating the combined mother liquors of dryness, dissolving the resulting residue in a mixture of ether/hexane 1:9 and separating the 10α-methyl derivative of formula IVa from the solution by chromatography over silica gel.

The pure 10β-methyl and 10α-methyl-4β-acetoxy compounds of formula IV or the corresponding 4β-hydroxy-, 4-keto- or 4α-hydroxy derivatives are submitted to an aminolysis by reacting same with a secondary amine $R_1$, preferably a cyclic amine such as, e.g., piperidine, morpholine, N-substituted piperazine or pyrrolidine. The reaction is preferably performed in the presence of a basic compound, such as sodium- or potassium hydrogen carbonate. A solvent, preferably an aprotic liquid, e.g., dimethyl formamide, dimethyl sulfoxide or hexamethyl phosphoric acid triamide may be added. The reaction temperature preferably is between about zero and about 200° C., especially about 25° to 180° C. Depending on the reaction conditions, an acetoxy group $R_3$, may be at least partially hydrolyzed during the reaction. The hydrolysis of the acetoxy group will be completed at the latest during the recovering of the resulting amine from the reaction mixture.

If desired, subsequent to the aminolysis the 4β-hydroxy group of the compounds of formula Ia may be further changed by transforming the same into an acylate or carbamate group in a conventional manner, or prior to the aminolysis, the hydroxy group may be changed into a keto group to form the corresponding decanone, and the 4-keto group may optionally be transformed into the 4α-hydroxy group, which in turn after the aminolysis may be further changed into an acylate- or carbamate group in a conventional manner.

The transformation of the 4β-hydroxy compound into the 4α-hydroxy compound by way of the intermediate 4-keto compound may be performed according to the general reaction sequence which is shown below.

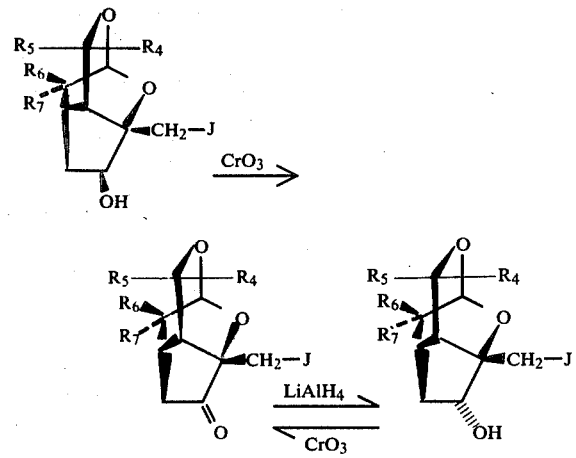

This transformation may be performed according to the methods as described in the German Offenlegungsschriften Nos. 2,547,205, 2,027,890 and 2,306,118, the disclosure of which is hereby incorporated by reference. This transformation can be effected either on the 3-halomethyl compounds of formula (III) or the corresponding final 3-aminomethyl compounds.

Except for the different positions of the 10-methyl groups, the substituents in the 3'-, 4- and 8-position may be varied in conventional manners, particularly the substituents in the 3'- and in the 4-position may be varied as described above and the substituent in the 8-position may be varied according to methods which are known from the prior art, e.g., are disclosed in the German Offenlegungsschrift No. 2,129,507, the disclosure of which is also hereby incorporated by reference.

The compounds of formula I can be recovered in free form or in form of a salt. A salt from can easily be transferred into the free form and vice versa in conventional manners. Acid addition salts of compounds of formula I can be formed with mineral acids such as, hydrochloric, hydrobromic, or sulfuric acid or with organic acids such as, maleinic or tartaric acid.

The compounds of formula I or their pharmaceutically acceptable salts may be formulated in conventional manners into pharmaceutical compositions optionally comprising an inert diluent and/or conventional pharmaceutical adjuvants.

Within the formula I, $R_1$ represents a disubstituted amino radical. Suitable substituents $R_1$ and di-lower alkylamino, and especially cyclic amino radicals, wherein the nitrogen preferably is a member of a heterocyclic containing 5 to 7 ring members which may contain a second heteroatom selected from the group of oxygen and monosubstituted nitrogen. Examples of such cyclic amino radicals are the piperidino, pyrrolidino, morpholino radicals.

The substituent in the 4-position of the 2,9-dioxatricyclo[4,3,1,0$^{3,7}$] decane preferably is hydroxy which preferably is in the β-position. The substituent in the 8-position of the 2,9-dioxatricyclo[4,3,1,0$^{3,7}$] decane preferably is a lower alkyloxy group, especially methoxy. If the substituent in the 8-position is aralkyloxy, it preferably is benzyloxy.

The new compounds of formula I according to this invention and their pharmaceutically acceptable salts exhibit valuable pharmacological properties and therefore are useful in medical treatment. In particular, they are useful as sedatives since they exhibit sedative activities in animals as is indicated in standard tests, e.g., they inhibit the motility in mice upon oral administration of from 1 to 100 mg/kg body weight.

The compounds of formula I according to this invention and their pharmaceutically acceptable salts are especially useful as soporific agents in the treatment of sleep disorders since they exhibit sleep-increasing and sleep-improving activities in animals as is indicated in standard tests. For example, they effect a significant increase of the duration of hexobarbital induced sleep in mice upon oral administration of from 1 to 100 mg/kg body weight. Electroencephalographical tests in rats show an increase of the classical and the paradoxical sleep phases upon oral administration of from 1 to 100 mg/kg body weight.

For the above mentioned uses, the administered doses can vary considerably depending on the type of the compound, the animal, the mode of administration, the treated conditions and the therapy which is desired. Usually, satisfactory results are obtained with dosages between 0.075 and 100 mg/kg body weight. These doses can be administered internally, preferably orally, or parenterally. For example, daily oral doses for larger mammals can be chosen between 5 and 50 mg.

The advantageous effects of the compounds according to the present invention on the classical and the paradoxical sleep phases which have been shown in rats by electroencephalography, combined with the other sedative properties of the compounds and their low toxicity fulfill the requirements which are postulated by the latest sleep research.

The surprising activity of the new compounds will be further explained using the piperidine derivative of formula II as an example.

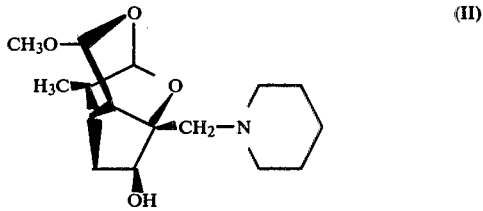

The hydrochloride of formula II, test substance number 1973, and the hydrogentartrate of formula II, test substance number 2961, have been used for pharmacological testing. During the screening in white mice, upon administration of oral dosages starting at 10 mg/kg, the compounds effect a remarkable increase of the duration of hexobarbital induced sleep, the degree of which depends upon the administered dose, but do not exhibit any anticonvulsive activity as the soporifics of the barbiturate or benzodiazepine type do.

The compounds also exhibit a motility inhibiting activity in mice. For this activity, the $ED_{50}$ is 3 mg/kg p.o.

This sedative activity has been confirmed in rats as well.

Upon observation of the sleep phases using the electroencephalography, the novel effect of the new compounds are seen: a strong increase of the paradoxical and the classical sleep phases and at the same time only a little decrease of the wake phase are observed upon oral administration of of 2.5 to 80 mg/kg body weight rate. These effects are found during a 4 hour observing period, as well as during an 8 hour observing period.

The toxicity of the hydrochloride of (II) in mice is as follows: $LD_{50}$ 1136 mg/kg p.o. and 406 mg/kg i.p.

The compounds of formula III may be prepared according to the general reaction sequence, which is shown below:

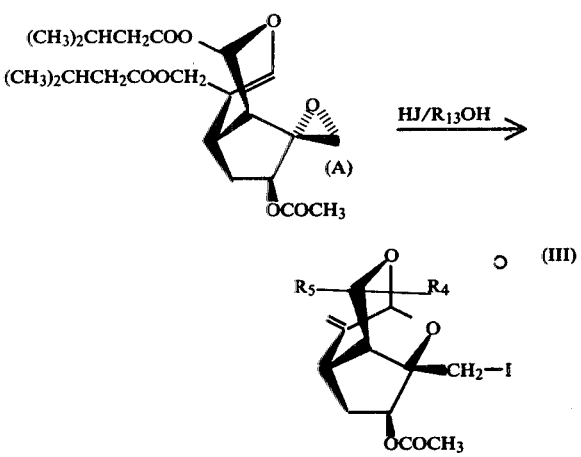

As is demonstrated in the above reaction sequence in a first step dihydrovaltratum of formula A, or an extract containing dihydrovaltratum, is reacted with a hydrogen iodide in an alcohol $R_{13}OH$, wherein $R_{13}$ is alkyl or aralkyl, whereby a mixture of two isomeric compounds of formula III are formed wherein either $R_4$ or $R_5$ represents the alkoxy or aralkyloxy group which corresponds to the alcohol $R_{13}OH$. This isomeric mixture is separated in a conventional manner.

The preparation of the compounds of formula III may, e.g., be performed as is described in the German Offenlegungsschrift No. 2,129,507, the disclosure of which is hereby incorporated by reference.

The invention will now be further described by the following examples.

EXAMPLE 1

Preparation of 3-piperidinomethyl-4β-hydroxy-8-methoxy-10β-methyl-2,9-dioxatricyclo[4,3,1,0$^{3,7}$] decanehydrogentartrate (VII) from 3-iodomethyl-4β-acetoxy-8-methoxy-10-methylene-2,9-dioxatricyclo[4,3,1,0$^{3,7}$] decane (V).

A. Preparation of 3-iodomethyl-4β-acetoxy-8-methoxy-10β-methyl-2,9-dioxatricyclo[4,3,1,0$^{3,7}$] decane (VI) from 3-iodomethyl-4β-acetoxy-8-methoxy-10-methylene-2,9-dioxatricyclo[4,3,1,0$^{3,7}$] decane (V).

A solution of 800 g of 3-iodomethyl-4β-acetoxy-8-methoxy-10-methylene-2,9-dioxatricyclo[4,3,1,0$^{3,7}$] decane in 3 liters of acetic acid ethyl ester is added to a prehydrogenated suspension of 35 g of platinum oxide in 300 ml of acetic acid ethyl ester and the mixture is hydrogenated at room temperature and normal pressure. At the beginning, the hydrogen uptake is rather fast, yet it becomes rather slow towards the termination of the reaction. After the theoretical amount of hydrogen (47.2 liters) has been taken up, the reaction mixture is filtered over asbestos under a nitrogen atmosphere. Upon evaporation of the solvent, 804 g of the hydrogenated raw product are obtained corresponding to 100% of the theoretical yield. After repeatedly recrystallizing this raw product from methanol several times, 542 g of the pure 10β-methyl compound of formula VI are obtained, corresponding to 67% of the theoretical yield relative to the amount of starting material V.

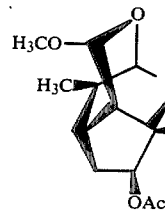

(VI)

Empirical formula:
$C_{13}H_{19}IO_5$
Molecular weight: 382.19
mp: 129°
$[\alpha]_D^{20} = +24.5°$ in methanol B. Preparation of 3-piperidinomethyl-4β-hydroxy-8-methoxy-10β-methyl-2,9-dioxatricyclo[4,3,1,0$^{3,7}$] decane (II) from (VI).

54 g of sodium hydrogen carbonate are suspended in a solution of 191 g of (VI) in 250 ml of piperidine. The suspension is heated to boiling temperature under thorough stirring and reflux condenser cooling. Within 30 minutes, the easily agitatable reaction mixture changes into a viscid slurry which gradually acquires a yellow color. After the aminolysis is terminated (=after about 4-5 hours) the reaction mixture is cooled to room temperature, 500 ml of water and then 200 ml of a 30% sodium hydroxide solution are added and the reaction mixture is extracted 4 times with 400 ml of ether each. The combined organic phases are dried, clarified over active carbon and evaporated under vacuum.

The resulting raw product is purified over silica gel using n-hexane/diethylamine as an eluating solvent.

Yield: 146.2 g corresponding to 98.3% of the theoretically obtainable amount.

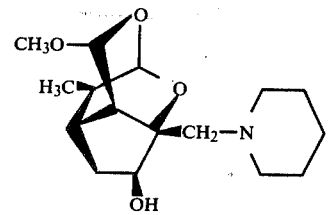

(II)

Empirical formula:
$C_{16}H_{27}NO_4$
Molecular weight: 297.4
mp: 60°–61° C. (recrystallized from petrol ether)
$[\alpha]_D^{20}$: –6.8° (in methanol)

C. Preparation of 3-piperidinomethyl-4β-hydroxy-8-methoxy-10β-methyl-2,9-dioxatricyclo-[4,3,1,0$^{3,7}$] decane hydrogentartrate (VII) from (II).

146.2 g of (II) are dissolved in 500 ml of ethanol then a solution of 72 g of L(+)-tartaric acid in 1,500 ml of ethanol are added, under thorough stirring. After precipitation of the precipitate, stirring is continued for another hour at a temperature of 0° C. and the precipitate is filtered and washed with cold ethanol. After drying at 60° C. under vacuum, 213 g of the white crystalline hydrogentartrate of (II) are obtained. This corresponds to 95% of the theoretically obtainable amount.

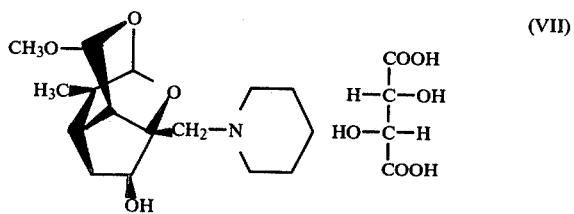

(VII)

Empirical formula:
$C_{20}H_{33}NO_{10}$
Molecular weight: 447.76
mp: 183° C.
$[\alpha]_D^{20} = -11.6°$ in methanol Analogous to Example 1A and B, the following substances are prepared; see Table I.

TABLE I

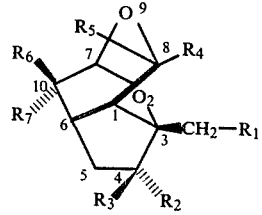

| $R_1$ | $R_2$ | $R_3$ | $R_4$ | $R_5$ | $R_7$ | $R_6$ | Empirical Formula | Molecular Weight |
|---|---|---|---|---|---|---|---|---|
| —N⟨O⟩ (morpholino) | H | OH | H | OCH$_3$ | H | CH$_3$ | $C_{15}H_{25}NO_5$ | 299.37 |
| —N⟨N—CH$_3$⟩ (N-methylpiperazino) | H | OH | H | OCH$_3$ | H | CH$_3$ | $C_{16}H_{28}N_2O_5$ | 312.41 |
| —N⟨N—Ph⟩ (N-phenylpiperazino) | H | OH | H | OCH$_3$ | H | CH$_3$ | $C_{21}H_{30}N_2O_4$ | 374.48 |

TABLE I-continued

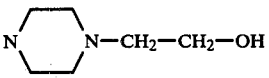

| R₁ | R₂ | R₃ | R₄ | R₅ | R₇ | R₆ | Empirical Formula | Molecular Weight |
|---|---|---|---|---|---|---|---|---|
| 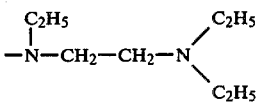 | H | OH | H | OCH₃ | H | CH₃ | $C_{17}H_{30}N_2O_5$ | 342.44 |
| 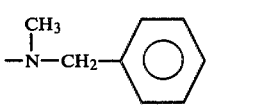 | H | OH | H | OCH₃ | H | CH₃ | $C_{20}H_{36}N_2O_4$ | 368.52 |
| 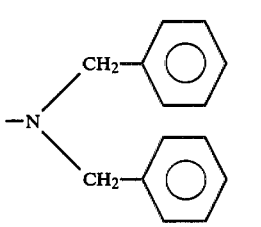 | H | OH | H | OCH₃ | H | CH₃ | $C_{19}H_{27}NO_4$ | 333.43 |
| 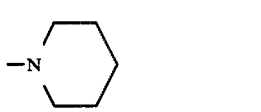 | H | OH | H | OCH₃ | H | CH₃ | $C_{25}H_{31}NO_4$ | 403.53 |
| 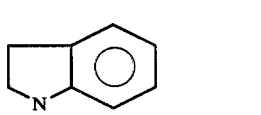 | H | OH | H | OCH₃ | H | CH₃ | $C_{17}H_{28}NO_4$ | 311.42 |
| 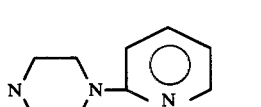 | H | OH | H | OCH₃ | H | CH₃ | $C_{18}H_{25}NO_4$ | 331.41 |
|  | H | OH | H | OCH₃ | H | CH₃ | $C_{20}H_{28}N_3O_4$ | 375.47 |
| 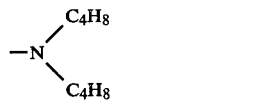 | H | OH | H | OCH₃ | H | CH₃ | $C_{15}H_{25}NO_4$ | 283.37 |
| 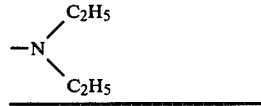 | H | OH | H | OCH₃ | H | CH₃ | $C_{18}H_{35}NO_4$ | 341.48 |
| −N(C₂H₅)₂ (C₂H₅, C₂H₅) | H | OH | H | OCH₃ | H | CH₃ | $C_{15}H_{27}NO_4$ | 285.38 |

Analogous to Example 1C, the following substances are prepared; see Table II.

TABLE II

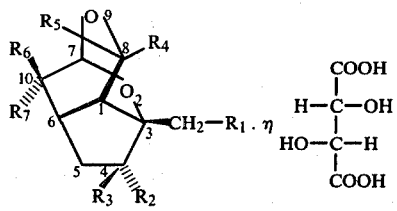

| R₁ | R₂ | R₃ | R₄ | R₅ | R₇ | R₆ | Empirical Formula | Molecular Weight |
|---|---|---|---|---|---|---|---|---|
| ![](piperazine-CH₂CH₂-OCO-N⁴ with C₂H₅) | H | OCONHC₂H₅ | H | OCH₃ | H | CH₃ | $C_{31}H_{52}N_4O_{19}$ | 784.77 |
| $C_2H_5$-N-CH₂-CH₂-N(C₂H₅)₂ | H | OCONH-C₂H₅ | H | OCH₃ | H | CH₃ | $C_{31}H_{57}N_3O_{18}$ | 775.78 |
| -N(piperidine) | OH | H | H | OCH₃ | H | CH₃ | $C_{20}H_{33}NO_{10}$ | 447.47 |
| -N(piperidine) | OCONH-CH(CH₃)₂ | H | H | OCH₃ | H | CH₃ | $C_{24}H_{40}N_2O_{11}$ | 532.58 |
| -N(piperidine) | OCONH-CH₂-CH=CH₂ | H | H | OCH₃ | H | CH₃ | $C_{24}H_{38}N_2O_{11}$ | 530.56 |
| -N(morpholine) | H | OH | H | OCH₃ | H | CH₃ | $C_{19}H_{31}NO_{11}$ | 449.46 |
| -N(pyrrolidine) | H | OH | H | OCH₃ | H | CH₃ | $C_{19}H_{31}NO_{10}$ | 433.45 |
| N(C₄H₉)₂ | H | OH | H | OCH₃ | H | CH₃ | $C_{23}H_{42}NO_{10}$ | 481.58 |

EXAMPLE 2

Preparation of 3-piperidinomethyl-4β-hydroxy-8-methoxy-10α-methyl-2,9-dioxatricyclo[4,3,1,0³,⁷] decane hydrogentartrate (VIIa)

A. Isolation of 3-iodomethyl-4β-acetoxy-8-methoxy-10α-methyl-2,9-dioxatricyclo[4,3,1,0³,⁷] decane (VIa) from the mother liquors obtained in Example 1A.

The combined mother liquors from the crystallization of (VI) in Example IA are evaporated. The residue, 250 g of a red-brownish oil, are dissolved in 700 ml of methanol and the solution is allowed to stand at a temperature of 0° C. for 24 hours. During this time, the remaining contents of the compound (VI) crystallize. The crystallizate (120 g corresponding to 14.9% of the theoretical yield relative to original 800 g of the starting material V) is filtered off and analyzed but is not utilized further within the procedure of Example 2. The crystallizate contains about 10% of the 10α-methyl epimer according to a determination by NMR-spectroscopy.

The filtrate is evaporated and the residue, 130 g of a red-brownish oil, is purified by chromatography over a column of 25 times its amount of silica gel, using a mixture of ether/hexane 1:9 as eluating liquid.

The purity of the various fractions is checked by thin layer chromatography. After combining and evaporating the fractions which have an enriched content of the compound (VIa), 80 g of a light yellow oil are obtained.

This oil is dissolved in a mixture of water/acetone 1:9. The saturated solution is cooled to 0° C. and crystallization is started by means of a seed crystal and scratching. After redissolving the precipitate and reprecipitating it twice, 53 g of the compound (VIa) (corresponding to 6.6% of the theoretical yield relative to the starting compound V), which is free of its epimer are recovered.

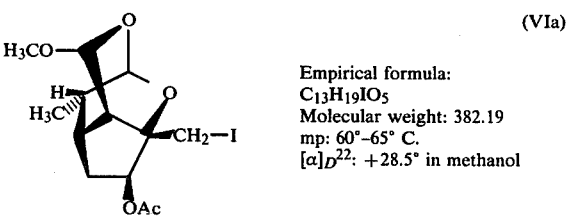

(VIa)

Empirical formula: $C_{13}H_{19}IO_5$
Molecular weight: 382.19
mp: 60°–65° C.
$[\alpha]_D^{22}$: +28.5° in methanol B. Preparation of 3-piperidinomethyl-4β-hydroxy-8-methoxy-10α-methyl-2,9-dioxatricyclo[4,3,1,0³,⁷] decane (IIa) from 3-iodomethyl-4β-acetoxy-8-methoxy-10α-methyl-2,9-dioxatricyclo[4,3,1,0³,⁷] decane (VIa).

The aminolysis of the compound VIa is effected according to the method which is described in Example 1B.

Yield: 40.8 g corresponding to 99% of the theoretical amount relative to the 53 g of the starting compound VIa.

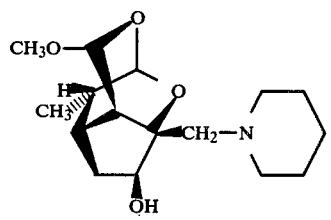

(IIa)

Empirical formula: $C_{16}H_{27}NO_4$
Molecular weight: 297.4
mp: $<0°$ C.
$[\alpha]_D^{20}$: $-7.5°$ in methanol C. Preparation of 3-piperidinomethyl-4β-hydroxy-8-methoxy-10α-methyl-2,9-dioxatricyclo[4,3,1,0$^{3,7}$] decane hydrogentartrate (VIIa) from (IIa).

A solution of 20 g L(+)-tartaric acid in 400 ml of ethanol is added to a solution of 40 g II a in 150 ml of ethanol. After the addition is finished, the reaction mixture is stirred during one hour at a temperature of 0° C. Then the mixture is filtered and the precipitate is washed with cold ethanol. The crystallizate is dried at 60° C. under vacuum. Yield: 57 g corresponding to 95% of the theoretically obtainable amount.

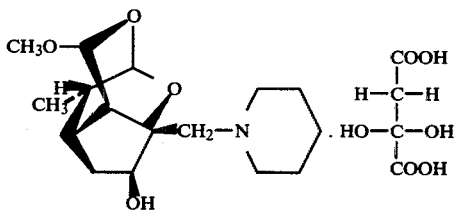

(VIIa)

Empirical formula:
$C_{20}H_{33}NO_{10}$
Molecular weight: 447.46
mp: 182°–185° C.
$[\alpha]_D^{20}$: $-11.9$ in methanol

EXAMPLE 3

Preparation of 3-piperidinomethyl-4β-phenylcarbamoyloxy-8-methoxy-10β-methyl-2,9-dioxatricyclo[4,3,1,0$^{3,7}$]-decane from (II).

5.0 g of (II) are dissolved in 10 ml of methylene chloride. 3 ml of phenyl isocyanate and 680 mg of phenylmercury acetate as a catalyst are added and subsequently the reaction mixture is refluxed for 1 to 2 hours. After adding 5 ml of methanol, the mixture is evaporated. The residue is dissolved in ether and treated with sodium sulfate and active carbon. After filtering the mixture, washing the filter residue with ether and evaporating the filtrate, 6.27 g of the crystalline phenyl carbonate are obtained. This corresponds to 90% of the theoretically obtainable amount.

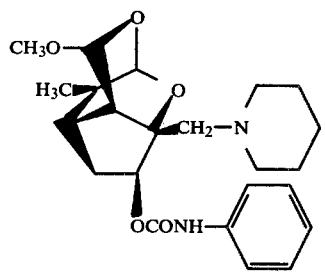

Empirical formula:
$C_{23}H_{32}N_2O_5$
Molecular weight: 416.52

EXAMPLE 4

Preparation of 3-morpholinomethyl-4β-benzoyloxy-8-methoxy-10β-methyl-2,9-dioxatricyclo[4,3,1,0$^{3,7}$] decane.

3.73 g of 3-morpholinomethyl-4β-hydroxy-8-methoxy-10β-methyl-2,9-dioxatricyclo[4,3,1,0$^{3,7}$] decane are dissolved in pyridine. 7.05 g of benzoic acid anhydride are added and the mixture is refluxed for 2 hours. After adding chloroform, the mixture is shaken with a 2 N solution of sodium carbonate. The organic phase is separated and washed with water once. The aqueous phases are separately extracted with chloroform twice each. The united organic extracts are treated with sodium sulfate and active carbon and filtered over theorite. After evaporating the filtrate, the residue is purified by column chromatography over silica gel using a mixture of 50% of ether in n-hexane as an eluating liquid. After evaporating the eluate, 2.9 g of the benzoate are crystallized from isopropanol. This corresponds to 57% of the theoretically obtainable amount.

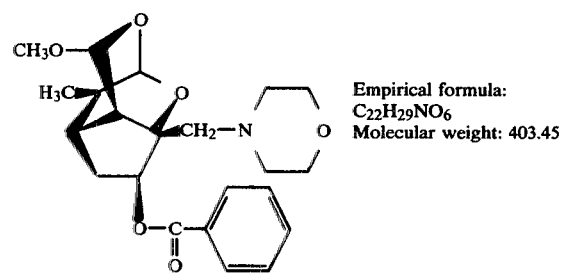

Empirical formula:
$C_{22}H_{29}NO_6$
Molecular weight: 403.45

EXAMPLE 5

Preparation of 3-piperidinomethyl-4β-hydroxy-8-methoxy-10β-methyl-2,9-dioxatricyclo[4,3,1,0$^{3,7}$] decane hydrochloride from (II).

5 g of (II) are dissolved in 50 ml of ether. Dry gaseous hydrogen chloride is passed through the solution, until no further precipitate is formed. The ether is decanted and the precipitate is triturated with another portion of ether which is free from hydrogen chloride. After filtering the precipitate by suction, washing it with ether and drying it, 5.4 g of the crystalline hydrochloride are obtained. This corresponds to 97% of the theoretically obtainable amount.

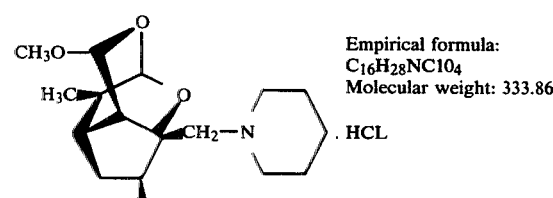

Empirical formula:
$C_{16}H_{28}NClO_4$
Molecular weight: 333.86

Analogous to Example 5, the following substances are prepared.

3-pyrrolidinomethyl-4β-hydroxy-8-methoxy-10-methyl-2,9-dioxatricyclo[4,3,1,0$^{3,7}$] decane hydrochloride, and 3-morpholinomethyl-4β-hydroxy-8-methoxy-10-methyl-2,9-dioxatricyclo[4,3,1,0$^{3,7}$] decane hydrochloride.

EXAMPLE 6

| CAPSULES FOR ORAL APPLICATION | |
|---|---|
| 3-piperidinomethyl-4β-hydroxy-8-methoxy-10β-methyl-2,9-dioxatricyclo[4,3,1,0³,⁷] decane hydrochloride | 20 g |
| lactose | 60 g |
| starch | 18.5 g |
| magnesium stearate | 1.5 g |

The components are thoroughly mixed and the mixture is filled into gelatin capsules in portions of 100 mg per capsule.

EXAMPLE 7

One capsule, which is prepared according to Example 6, is administered to an adult person at night for the treatment of sleep disorders.

EXAMPLE 8

Preparation of 4-acetoxy-8-hydroxy-3-iodomethyl-10-methylene-2,9-dioxatricyclo[4,3,1,0³,⁷] decane (III) from a 66% strength dihydrovaltrate extract.

425 g of extract were dissolved in one liter of acetic acid at 60° C., then a mixture of 130 ml of hydriodic acid (57% strength) and 1 liter of water were added to the solution, and the mixture was left to stand for 2 hours at 60° C., with occasional stirring.

Working up

Afte addition of 100 g of acetivated charcoal, suction filtration over Theorit (tradename—fire resistant asbestos wool) was effected, following by thorough washing with 4 liters of ether. 3 liters of water were added to the filtrate, thorough shaking was effected, and the ether phase was separated off. This was then washed with alkaline, once with 2 liters of water and once with soda solution (1.5 kg of sodium carbonate in 8 liters of water). The three water phases were then extracted individually 3 times with, in each case, 2 liters of ether. The combined ether phases were dried over 1 kg of sodium sulfate, treated with 100 g of activated charcoal, suction filtered over Theorit and then concentrated in a vacuum at 30°–40° C. in a round flask, with addition of 18 ml of water; II recrystallized. After rubbing with ether and filtration over a suction filter, 170 g of crude crystalline product were obtained representing 70% of the theoretical yield.

Empirical formula: $C_{12}H_{15}O_5I$; Molecular weight: 366.14; mp: 152°–156° C. (Kofler, uncorrected); $[\alpha]_C^{+22° C.}$: +142° (methanol).

While the invention has now been described in terms of various preferred embodiments, the skilled artisan will readily appreciate that various substitutions, modifications, changes, and omissions may be made without departing from the spirit thereof. Accordingly, it is intended that the scope of the present invention be limited solely by that of the following claims.

What is claimed is:

1. A process for preparing compounds of formula Ia

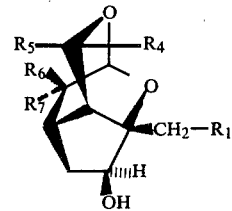

wherein
$R_1$ represents a tertiary amino group;
one of $R_4$ and $R_5$ is hydrogen and the other represents alkyloxy or aralkyloxy; and
one of $R_6$ and $R_7$ is hydrogen and the other represents methyl, which comprises the steps of
(a) catalytically hydrogenating a compound of formula III

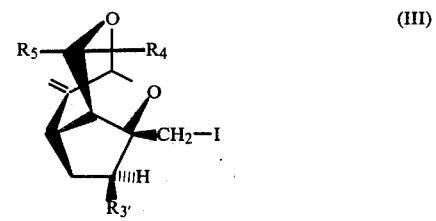

wherein $R_{3'}$ represents acetoxy and $R_4$ and $R_5$ are as defined above by means of hydrogen in the presence of platinum oxide to form a mixture of epimeric compounds of formula IV

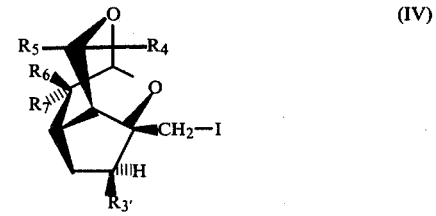

wherein $R_{3'}$, $R_4'$, $R_5'$, $R_6$ and $R_7$ are as defined above, comprising a 10α-methyl epimer of formula IVa and a 10β-methyl epimer of formula IVb

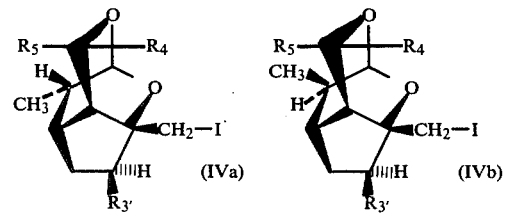

wherein $R_{3'}$, $R_4$ and $R_5$ are as defined above;
(b) separating the compounds of formula IVb and IVa from said mixture;
(c) recovering at least one of the compounds of formula IV substantially free from its epimer;
(d) reacting said compound of formula IV with a secondary amine $R_1$ and subjecting it to ester-hydrolysing conditions, whereby a reaction mixture comprising the compound of formula Ia substantially free from its epimer is obtained; and (e) recovering the compound of formula Ia from said reaction mixture.

2. The process as defined in claim 1, wherein $R_1$ represents a group

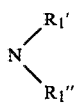

wherein $R_1'$ and $R_1''$ are the same or different and each represents an alkyl group containing 1 to 6 carbon atoms, a phenylalkyl group containing 7 to 9 carbon atoms, or $R_1'$ and $R_1''$ together with the nitrogen atom to which they are bound form a cyclic radical selected from the group consisting of indolinyl and radicals of the formula

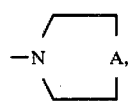

wherein A represents a bond, one or two alkyl chains each containing 1 to 3 carbon atoms, oxygen or a group $>$N-A', wherein A' represents an alkyl group containing 1 to 4 carbon atoms which is unsubstituted or substituted in the ω-position by a substituent which is selected from the group consisting of hydroxy, acyloxy and carbamyloxy, pyridyl or a phenyl or benzhydryl group, the phenyl rings of which are unsubstituted or substituted by halogen.

3. The process as defined in claim 1, wherein one of $R_4$ and $R_5$ is hydrogen and the other represents an alkoxy group containing 1 to 6 carbon atoms or an aralkyloxy group containing 7 to 9 carbon atoms.

4. The process as defined in claim 2, wherein $R_1'$ and $R_1''$ are the same or different and each represent alkyl containing 1 to 6 carbon atoms or benzyl.

5. The process as defined in claim 2, wherein the amine $R_1$ is selected from the group consisting of cyclic amines containing 5 to 7 carbon atoms and piperazine derivatives, the 4-nitrogen atom of which is monosubstituted.

6. The process as defined in claim 5, wherein the amine $R_1$ is piperidino.

7. The process as defined in claim 1, which further comprises the step of esterifying the compound of formula Ia whereby a compound of formula Ib is formed

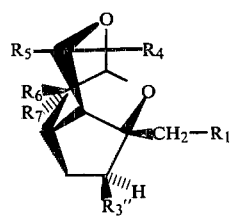

(Ib)

wherein $R_1$, $R_4$, $R_5$, $R_6$ and $R_7$ are as defined above, and $R_3''$ represents acyloxy or carbamyloxy.

8. The process as defined in claim 7, wherein $R_3''$ represents an acyloxy group Z—COO—, wherein Z is alkyl or alkenyl containing 1 to 4 carbon atoms or phenyl, or a carbamyloxy group Z—NHCOO—, wherein Z is alkyl or alkenyl containing 1 to 4 carbon atoms or phenyl.

9. The process as defined in claim 1, wherein the reacting step (d) further comprises the step of hydrolyzing the O—COCH$_3$ of the compound of formula IV, whereby a compound of formula IVc is formed

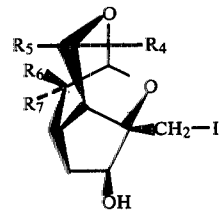

(IVc)

wherein $R_4$, $R_5$, $R_6$ and $R_7$ are as defined above.

10. The process as defined in claim 9, which further comprises the steps of oxidizing the compound of formula IVc into a compound of IVd

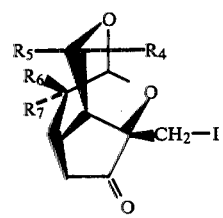

(IVd)

wherein $R_4$, $R_5$, $R_6$ and $R_7$ are as defined above, and reacting said compound of formula IVd with the secondary amine $R_1$ to form a compound of formula Ic

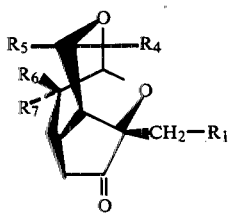

(Ic)

wherein $R_1$, $R_4$, $R_5$, $R_6$ and $R_7$ are as defined above.

11. The process as defined in claim 10, which further comprises the steps of reducing the compound of formula IVd into a compound of formula IVe

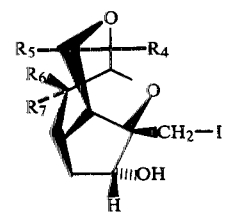

(IVe)

wherein $R_4$, $R_5$, $R_6$ and $R_7$ are as defined above, and reacting said compound of formula IVe with the secondary amine $R_1'$ to form a compound of formula Id

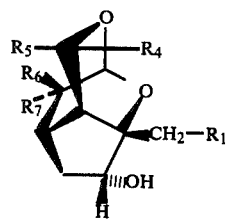

(Id)

wherein $R_1$, $R_4$, $R_5$, $R_6$ and $R_7$ are as defined above.

12. The process as defined in claim 11, which further comprises the step of esterifying the compound of formula Id, whereby a compound of formula Ie is formed

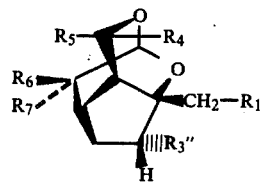

(Ie)

wherein $R_1$, $R_{3''}$, $R_4$, $R_5$, $R_6$ and $R_7$ are as defined above.

13. The process as defined in claim 1, wherein the hydrogenation is effected in the presence of a solvent.

14. The process as defined in claim 13, wherein the solvent is ethyl acetate, methanol, ethanol, or propanol.

15. The process as defined in claim 1, wherein the separating step (c) comprises the steps of crystallizing the 10β-methyl compound of formula IVb to form the crystallizate and a mother liquor, separating the crystallizate from the mother liquor, repeatedly redissolving and recrystallizing the compound of formula IVb to form a crystallizate and a mother liquor and separating the crystallizate from the mother liquor, combining the mother liquors from the repeated crystallizing operations, recovering a residue from the combined mother liquors, and separating the 10α-methyl compound of formula IVa from the residue by means of chromatography.

16. The process as defined in claim 15, wherein the crystallization is effected in methanol.

17. The process as defined in claim 15, wherein the chromatographical separation is effected over silica gel using a mixture of ether and hexane as a solvent.

* * * * *